(12) United States Patent
Kearns et al.

(10) Patent No.: US 7,978,085 B1
(45) Date of Patent: Jul. 12, 2011

(54) HUMAN AND PHYSICAL ASSET MOVEMENT PATTERN ANALYZER

(75) Inventors: William D. Kearns, Tampa, FL (US); James L. Fozard, Palm Harbor, FL (US); Eleftherios Kostis, Tampa, FL (US)

(73) Assignees: University of South Florida, Tampa, FL (US); CompData Systems, Inc., Tarpon Springs, FL (US)

( * ) Notice: Subject to any disclaimer, the term of this patent is extended or adjusted under 35 U.S.C. 154(b) by 248 days.

(21) Appl. No.: 12/396,002

(22) Filed: Mar. 2, 2009

Related U.S. Application Data (60) Provisional application No. 61/032,695, filed on Feb. 29, 2008.

(51) Int. Cl.
*G08B 23/00* (2006.01)

(52) U.S. Cl. .............. 340/573.4; 340/539.13; 340/572.1; 340/572.4

(58) Field of Classification Search ............... 340/573.4, 340/573.1, 539.12, 539.13, 572.1, 572.4, 340/825.49; 600/300, 301; 128/903, 920
See application file for complete search history.

(56) References Cited

U.S. PATENT DOCUMENTS

| | | | |
|---|---|---|---|
| 5,764,283 A | 6/1998 | Pingali et al. | |
| 6,611,206 B2 | 8/2003 | Eshelman et al. | |
| 6,968,294 B2 | 11/2005 | Gutta et al. | |
| 7,200,266 B2 | 4/2007 | Ozer et al. | |
| 7,248,933 B2 * | 7/2007 | Wildman | 700/90 |
| 7,307,523 B2 | 12/2007 | Kister et al. | |
| 7,432,810 B2 * | 10/2008 | Menache et al. | 340/572.1 |
| 2003/0191406 A1 | 10/2003 | Eberhart et al. | |
| 2004/0021569 A1 * | 2/2004 | Lepkofker et al. | 340/568.1 |
| 2004/0044293 A1 | 3/2004 | Burton | |
| 2004/0135694 A1 * | 7/2004 | Nyfelt | 340/573.1 |
| 2004/0174264 A1 * | 9/2004 | Reisman et al. | 340/573.4 |
| 2006/0190419 A1 | 8/2006 | Bunn et al. | |
| 2007/0139207 A1 | 6/2007 | Agapi et al. | |

OTHER PUBLICATIONS

Pavel, M.; Hayes, T.; Tsay, I.; Erdogmus, D.; Paul, A; Larimer, N.; Jimison, H.; Nutt, J. 2007.Continuous Assessment of Gait Velocity in Parkinson's Disease from Unobtrusive Measurements. Neural Engineering. CNE '07. 3rd International IEEE/EMBS Conference on, pp. 700-703, May 2-5, 2007.

* cited by examiner

*Primary Examiner* — Hung T. Nguyen
(74) *Attorney, Agent, or Firm* — Courtney M. Dunn; Smith & Hopen, P.A.

(57) ABSTRACT

A system of tracking and analyzing the movement of human subjects. UWB is used to track the location of all persons and/or physical objects (assets) occupying a defined area, giving their location with an accuracy of under twenty centimeters, their acceleration, their path, and a time/date-stamp for each observation. The system then uses artificial intelligence to detect variations in patterns of movement of designated individuals and movable physical objects in the defined space. The extracted patterns inform the design of intelligent methods to automatically track behavioral markers of movement. The system can be used to detect dementia in otherwise healthy human subjects and to identify changes in movement pursuant to medication or health changes and which may precede a fall or to detect proper movement in military training scenarios such as battlefield simulations.

16 Claims, 5 Drawing Sheets

| Participant | Age | MMSE score | Fractal D score |
|---|---|---|---|
| 1† | 91 | 8 | 1.68 |
| 2 | 63 | 14 | 1.59 |
| 3 | 64 | 19 | 1.84 |
| 4† | 93 | 19 | 1.27 |
| 5* | 73 | 20 | 1.30 |
| 6† | 92 | 20 | 1.44 |
| 7† | 84 | 20 | 1.54 |
| 8 | 88 | 21 | 1.19 |
| 9 | 88 | 21 | 1.79 |
| 10† | 88 | 21 | 1.62 |
| 11* | 75 | 24 | 1.35 |
| 12† | 79 | 25 | 1.26 |
| 13† | 86 | 25 | 1.24 |
| 14† | 88 | 28 | 1.41 |

* male
† wheelchair user

HUMAN AND PHYSICAL ASSET MOVEMENT PATTERN ANALYZER

CROSS REFERENCE TO RELATED APPLICATIONS

This application claims priority to currently U.S. Provisional Patent Application No. 61/032,695, filed Feb. 29, 2008.

STATEMENT OF GOVERNMENT INTEREST

This invention was made with Government support under Grant No. 071123 ARG-2007-34(Kearns USF) awarded by the Johnnie B. Byrd, Sr. Alzheimer's Institute. The Government has certain rights in the invention.

FIELD OF INVENTION

This invention relates to the use of ultra-wideband technology to track and analyze individuals and objects in a given area.

BACKGROUND

Wandering is a severe risk factor for persons with dementia and other psychiatric disorders. It is estimated that over six million Americans have dementia and wandering may occur in as many as sixty percent of dementia patients during their disorder. Wandering by a person with dementia or other psychiatric disorders can be dangerous and can lead to injury or even death due to falls, accident and/or exposure.

There are a number of anti-wandering technologies available to prevent wandering: pressure activated alarms, which sound when a pad, mat, or pillow is depressed as a subject attempts to leave a confined area; pull tab alarms, which sound when a tab is removed from the device; audible door alarms, which activate when a monitored door is accessed; optically-activated alarms, which activate when motion is detected; and visual deterrents, which are visual obstacles used to prevent access to forbidden areas.

These technologies provide the ability to track and locate a wandering subject. However, these tracking systems have a number of drawbacks. First, they rely primarily on alarms, which can lead to agitation in a wandering subject. Additionally, alarms have little or no use to a caregiver or wandering subject whose hearing is poor. Second, the tracking systems are subject to accidental triggering. For instance, a house pet may set them off and many of the tracking systems do not have sensitivity adjustments. Third, tracking systems may fail to give accurate vector information for proper tracking of the wandering subject.

Dementia and wandering behavior are independent predictors of falls of nursing home residents. While gait and balance disturbances have been precisely quantified using devices such as gait mats and accelerometers (J. L. Fozard, Sensory and Cognitive Changes With Age, in M. P. K. W. Schaie, Ed., *Mobility and transportation in the elderly*, New York: Springer, pp. 1-44 (2000); W. J. Evans, Effects of Exercise on Body Composition and Functional Capacity of the Elderly, in M. P. K. W. Schaie, Ed., Mobility and transportation in the elderly, New York: Springer, pp. 71-90 (2000); G. Allah, R. W. Kressig, F. Assal, F. R. Herrmann, V. Dubost, & O. Beauchet, Changes in gait while backward counting in demented older adults with frontal lobe dysfunction, *Gait & Posture,* 26(4), pp. 572-576 (2007); J. Verghese, J., R. B. Lipton, C. B. Hall, G. Kuslansky, M. J. Katz, & H. Buschke, Abnormality of gait as a predictor of non-Alzheimer's dementia, *New England Journal of Medicine,* 347(22), pp. 1761-1768 (2002)), detecting and quantifying wandering behavior within everyday movements has remained a challenging task because it occurs over large areas. Wandering is defined as repetitive or random variations in unconstrained voluntary movements. Wandering can manifest during goal-directed movements, e.g., traversing the bedroom to the bathroom, and in aimless movements. A key feature of wandering is path variability across an open field, a dimension not usually measured in laboratory-based studies of gait, which have traditionally focused on gait consistency in a prescribed course.

Past attempts to measure wandering have limitations. Using well-trained human observers, a behavioral rating scale has been developed allowing classification of different wandering patterns in open field situations. While successful, applications of this technology are usually obtrusive, require vigilant observers, and necessarily restrict the range in which observations are feasible. Algase and colleagues have compared the effectiveness of four accelerometer-based devices to detect wandering while simultaneously categorizing behavior using trained observers; the best of the four devices accounted for about 69% of the variance in observer-defined wandering. D. L. Algase, E. R. Beattie, S. A. Leitsch, C. A. Beel-Bates, *Am. J. of Alz. Dis. & Oth. Dem.* 18, 85-92 (2003).

In 2006, Teicher et al. used actigraphy in psychomotor assessment to diagnose psychiatric disorders including motor retardation, hyperactivity, catatonia, and early morning awakening. Teicher, M. H., McGreenery, C. E., & Ohashi, K., Actigraph assessment of rest-activity disturbances in psychiatric disorders: Psychosomatic Medicine, *Proceedings of the 18th World Congress on Psychosomatic Medicine* (pp. 32-37), International Congress Series. Teicher et al. identified total activity level, presence of sleep, and disturbed sleep-wake or rest-activity cycles as defining features of different disorders. The method used accelerometers on the body to continuously sample and store limb and trunk movements; however, it did not provide vector information.

These devices and methods have limitations and do not provide subject location and vector data, which is necessary to understand the variability in the paths taken by wandering subjects. Therefore, an automated assessment of episodic movements is needed that includes vector and duration information comparable or exceeding those derivable from accelerometry and gait mats.

SUMMARY OF INVENTION

The present invention improves upon actigraphy by adding direction (vector), duration, and rate and onset of gross motor movement episode to acceleration data. It accomplishes this through the use of ultra-wideband (UWB) sensor technology. The use of UWB presents a number of advantages, including the ability to filter out high frequency, low intensity accelometric transients characterizing small limb movements and the ability to vary the data-sampling rate to permit different levels of analysis.

The present invention includes a method of tracking and analyzing movement of human subjects. In an embodiment, a number of ultra-wideband (UWB) radio sensors are placed within a designated space. An origin location is then determined within this space. A plurality of UWB transponders, which provide location parameters in three planes (x, y, and z), are affixed to a number of human subjects. The location parameters of each of the subjects are collected at predetermined time intervals using the sensors, and then movement paths, which comprises the location parameters from each period of movement of each subject, are determined. The movement paths are then analyzed for Fractal D tortuosity characteristics, a spatial scale is chosen, Fractal D for the movement paths of each subject is estimated, and the average of the estimated Fractal Ds is calculated for each of the movement paths for each subject to produce a single Fractal D score for each subject. A high Fractal D score corresponds to a high likelihood of agitated movement and a greater value of the Fractal D score corresponds to a greater degree of agitated movement.

It may be necessary to remove location parameters that represent impossible movement, remove location parameters that represent movement outside the designated space, and/or remove location parameters that represent non-movement for a predetermined time.

In another embodiment, the fractal D tortuosity characteristics and cognitive status of the subjects are correlated.

The present invention also includes a method of detecting cognitive impairment in otherwise healthy human subjects. The cognitive impairment may be attributable to medication changes or health status. In an embodiment, UWB radio sensors are placed within a designated space such that the majority of the daily movements of the subjects to be studied are captured by the sensors. An origin is then determined within the space. UWB transponders that provide location parameters in three planes (x, y, and z) are affixed to each subject. The location parameters of each of the subjects are collected from the transponders at predetermined time intervals using the sensors. Movement paths for each subject are then determined from the location parameters. Each movement path comprises the location parameters from each period of movement of each subject. The movement paths are then analyzed for Fractal D tortuosity characteristics, the appropriate spatial scale is chosen, Fractal D for each of the movement paths of each subject is estimated, and the average of the estimated Fractal Ds for each of the movement paths for each subject is calculated to produce a single Fractal D score for each subject. A high Fractal D score corresponds to a high likelihood of dementia and a greater value of the Fractal D score corresponds to the a greater degree of dementia.

It may be necessary to remove location parameters that represent impossible movement, remove location parameters that represent movement outside the designated space, and/or remove location parameters that represent non-movement for a predetermined time.

In another embodiment, the fractal D tortuosity characteristics and cognitive status of the subjects are correlated.

The accuracy of the location parameters may be within about twenty centimeters and collection may occur about every 0.4 seconds. The Fractal D spatial scale is adjustable.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The system of the present invention gathers real-time locomotor data from persons and physical objects (assets) occupying defined working or congregate living settings such as nursing homes. Ultra-wideband (UWB) technology is used to track the location of all individuals and objects, giving their location with an accuracy of under twenty centimeters, their acceleration, their path, and a time/date-stamp for each observation to within 0.1 second (Ubisense, 2008). The system then uses artificial intelligence (AI) to detect variations in patterns of movement of designated individuals and movable physical objects in the defined space. The extracted patterns inform the design of intelligent methods to automatically track behavioral markers of movement.

UWB transponders are capable of precisely tracking the location of persons' and/or assets inside buildings to within twenty centimeters under laboratory conditions, allowing the variability in naturally occurring wandering behavior to be quantified in Assisted Living Facilities (ALF) and other settings with minimally obtrusive sensor systems. Because wandering involves changes in the directions of successive movement patterns at various spatial scales, fractal analytic techniques, like those employed to study gait variability, are used in the present method to successfully characterize wandering.

Fractal dimension (Fractal D) is the continuous analogue of geometrical dimensions. Thus for lines, Fractal D ranges from a minimum of 1, when the line is straight, to maximum of 2 when the line is so tortuous as to completely cover the plane. A person that is confused and wandering would be expected to have a tortuous path and thus a high Fractal D. The measured value of Fractal D also depends on the spatial scale being examined. A person who is walking down a corridor, but turning every now and then to investigate something, would have a movement path with a low Fractal D at large spatial scales and a high Fractal at small spatial scales. Thus, the choice of an appropriate spatial scale is essential.

Figure 1:
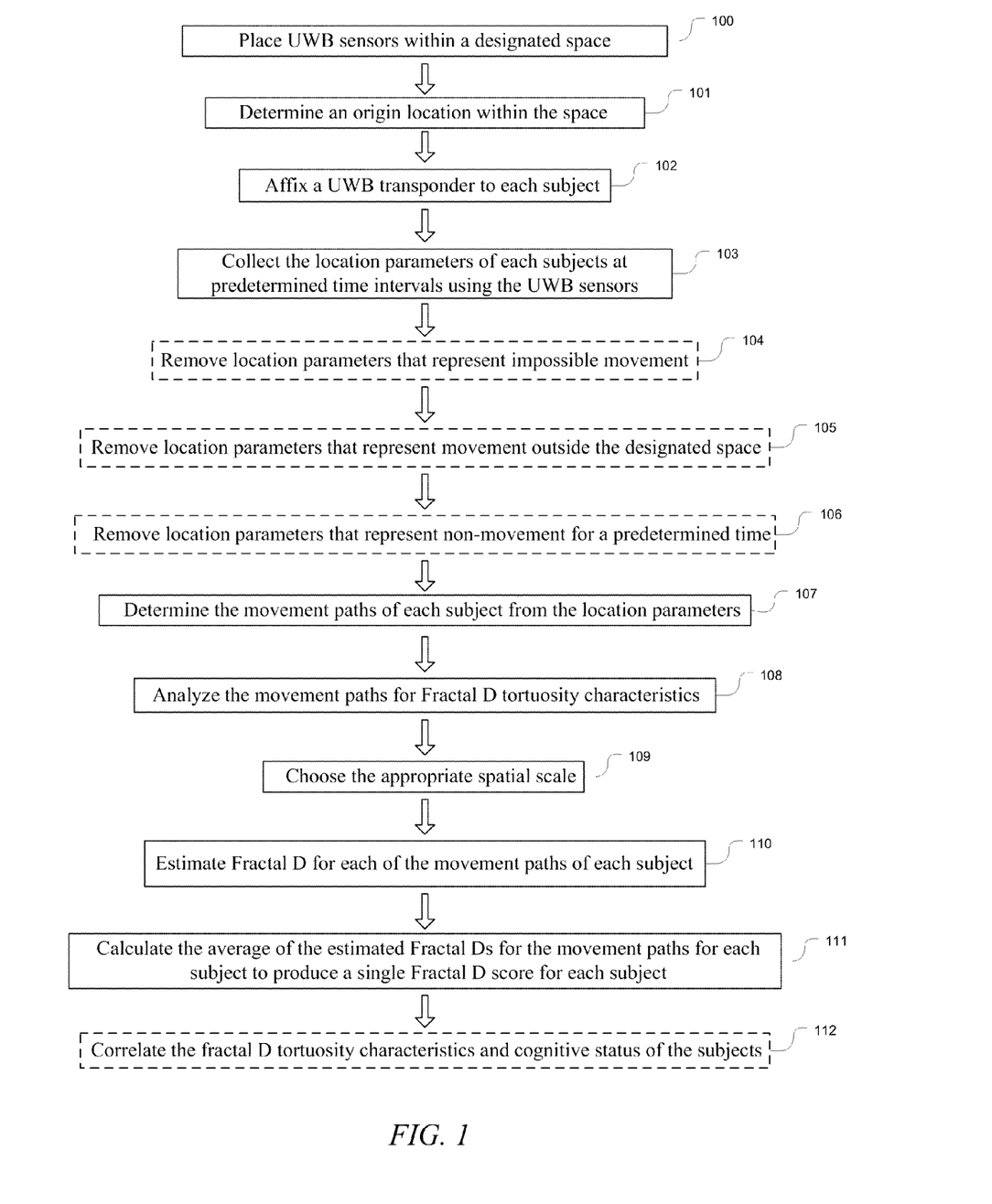
FIG. 1 is a flowchart of the system in accordance with an embodiment of the present invention.

FIG. 1 is a flowchart generally outlining an embodiment of the present invention. In operation 100, a number of UWB radio sensors are placed within a designated space. An origin location is then determined within this space in operation 101. In operation 102, a plurality of UWB transponders, which provide location parameters in three planes (x, y, and z), are affixed to a number of subjects (human or physical objects). The location parameters of each of the subjects are collected at predetermined time intervals using the sensors in operation 103.

Optionally, unwanted location parameters may then be removed in operations 104, 105, and 106. These unwanted location parameters may include location parameters that represent impossible movement (operation 104), location parameters that represent movement outside the designated space (operation 105), and location parameters that represent non-movement for a predetermined time (operation 106).

Then, movement paths, which are comprised of the location parameters from each period of movement of each subject, are determined in operation 107. The movement paths are analyzed for Fractal D tortuosity characteristics in operation 108, a spatial scale is chosen in operation 109, Fractal D for the movement paths of each subject is estimated in operation 110, and the average of the estimated Fractal Ds is calculated for each of the movement paths for each subject to produce a single Fractal D score for each subject in operation 111. The calculation performed in operation 111 may be for any interval including daily, weekly, or monthly intervals. A high Fractal D score corresponds to a high likelihood of agitated movement and a greater value of the Fractal D score corresponds to a greater degree of agitated movement. Optionally, the fractal D tortuosity characteristics and cognitive status of the subjects are then correlated in operation 112.

Although the invention has a large number of potential applications in which the location of people and objects is tracked in defined spaces, it was designed for two specific markets: (I.) congregate living settings for elderly persons, e.g., nursing home (NH) and assisted living facilities (ALF); and (II.) military training and monitoring applications. Both applications use the same hardware but slightly modified AI's. A virtual display of the movements of people and objects provides a continuous record similar in many respects to that provided by surveillance cameras or other technologies. A unique feature of the present invention is the use of AI to analyze complex patterns of movements. The following paragraphs describe these two applications in greater detail.

I. Congregate Living Settings: Nursing Homes and Assisted Living Facilities

The invention has four major features designed to provide: (1) state of the art management tools related to patient safety and security and the management of human subjects, e.g., designated clinical specialists, and machine assets, e.g., defibrillators or other emergency equipment; (2) clinically significant data that describes locomotor patterns characteristic of dementia and changes in health and medication, common in residents in both NH and ALF; (3) a multipurpose research tool for researchers working in NH/ALF settings; and (4) a tool based on location aware services to evaluate the effectiveness of machine generated messages or other interventions contingent on the location of a person.

The first major feature of the invention is its use of location-based services technology to manage patient safety and security. Because the technology localizes a subject in three dimensions with an error of less than twenty centimeters, the system can perform standard security functions accomplished by advanced standalone systems currently in use in formal care environments (Care-Trak, Roam Alert). The tracking technology on which the invention is based was developed for simultaneous large-scale inventory management and can be used for that purpose unmodified if the user so desires.

The second major feature analyzes locomotor patterns using AI and feeds the output to the subject's electronic medical record maintained at their NH or ALF. The AI differentiates locomotor behaviors indicative of depression, health, medication changes, and dementia and forms the core of a real-time health monitoring system. Dementia wandering locomotor patterns detected by the invention include lapping, pacing, and other repetitive locomotor features. Uni-polar depression patterns include heightened activity compared to elderly controls and an acrophase occurring later in the diurnal cycle of wandering and depression as they emerge in elders living in formal care settings.

The third major feature is a multipurpose research tool for the scientific community that conducts research in NH/ALF settings. Currently actigraphy has been one of the most heavily used research tools in NH/ALF settings yielding data on the amount of movement occurring over time, but providing no vector data. The present system yields information about direction, acceleration, and duration (vector) of gross locomotor activity in NH/ALF resident populations and can gather data continuously for periods exceeding one year while having superior sensitivity to locomotor patterns. This approach compensates for accelerometry's technical limitations: distinguishing high frequency signal components associated with small random arm or leg movements from similar signals indicative of gross body movement. The invention can also yield valuable data in investigations of pharmaceutical and behavioral interventions and interactions. It also allows efficacious study of patient-patient and patient-staff interactions and permits evaluation of the effects of changes in staffing patterns and physical NH/ALF layout on behavior and subsequent health.

The fourth feature of this technology includes evaluating the effectiveness of location-based services in which elders receive prompts or cues contingent upon activities or failure to complete activities (a field known as cognitive orthotics). For example, the present invention can assess the behavioral effectiveness of some second device, which presents voiced cues at specific locations to influence wandering behaviors.

Example

Congregate Living Setting

The method of the present invention was used to show that variability in movement paths in elderly subjects increased in subjects with lower measures of cognitive functioning. Using a commercially available tracking technology, movement data on fourteen subjects was obtained in their assisted living facility over a period of thirty days. One participant was fully ambulatory, eight participants used wheelchairs, and five participants used a rolling walker. Data on their precise location within an approximately nine meter by twenty-five meter monitored area was gathered. Using fractal mathematics to blindly calculate a measure of path tortuosity from subjects' movement data (Fractal D), the outcome of the participants' Mini Mental State Exam (MMSE) were predicted. The participants actual MMSE scores, obtained at the end of the study, matched the prediction even though MMSE scores are unrelated to the amount of movement an individual makes.

Figure 2:
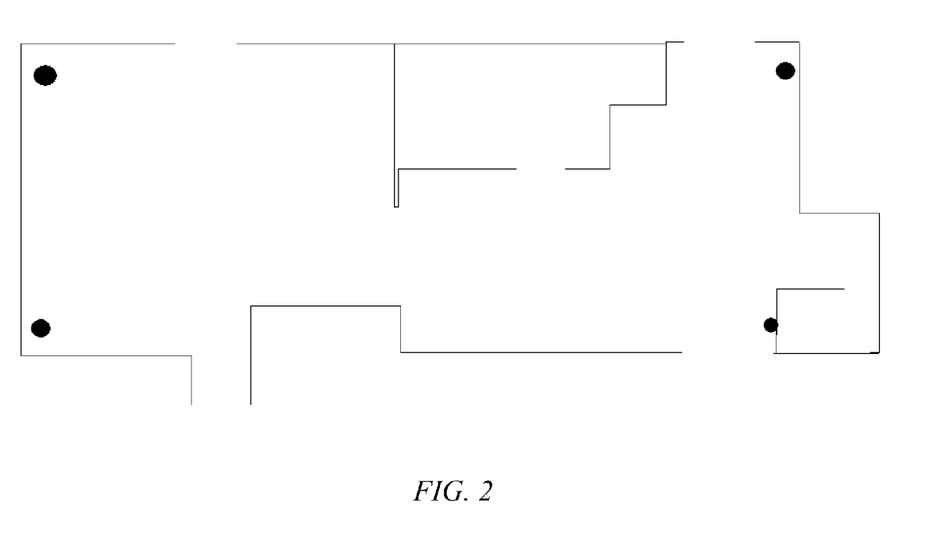
FIG. 2 is a diagram of an area used in an example of an application of the present invention showing the location of four ultra-wideband (UWB) sensors.

Four Ubisense 2.0 sensors were installed at each corner of an approximately rectangular (25.6 meters by 9.3 meters) common space that interconnected two dormitory wings an exterior exit and a dining room where all subjects ate their meals. The location of the sensors is shown in the diagram of FIG. 2. Tags were attached after the subjects' morning meal and medications and surrendered before the subjects retired. When in motion, the tags transmitted x, y, and z coordinates in meters once every 0.43 seconds relative to an origin set in one corner of the room.

Figure 3A:
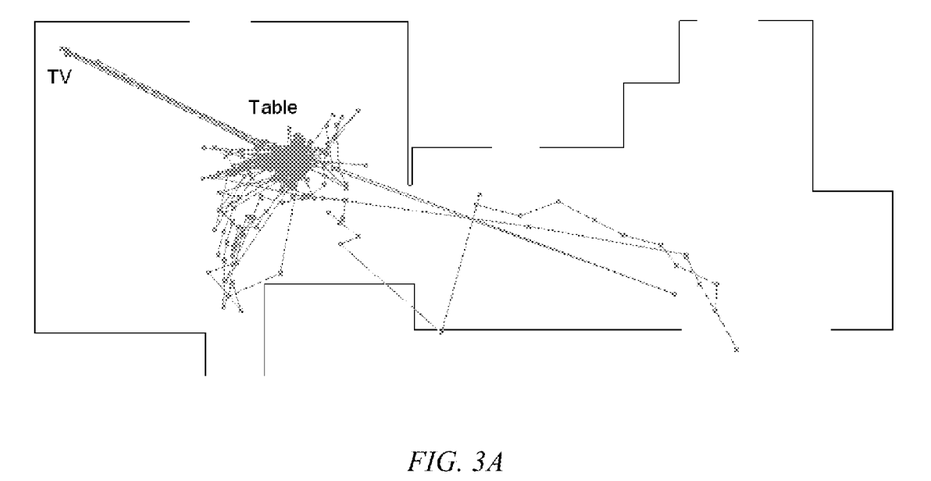
FIGS. 3A and 3B are diagrams of an area used in an example of an application of the present invention each showing the paths taken by a first subject on two different days. Each diagram represents the paths taken on a single day.
Figure 3B:
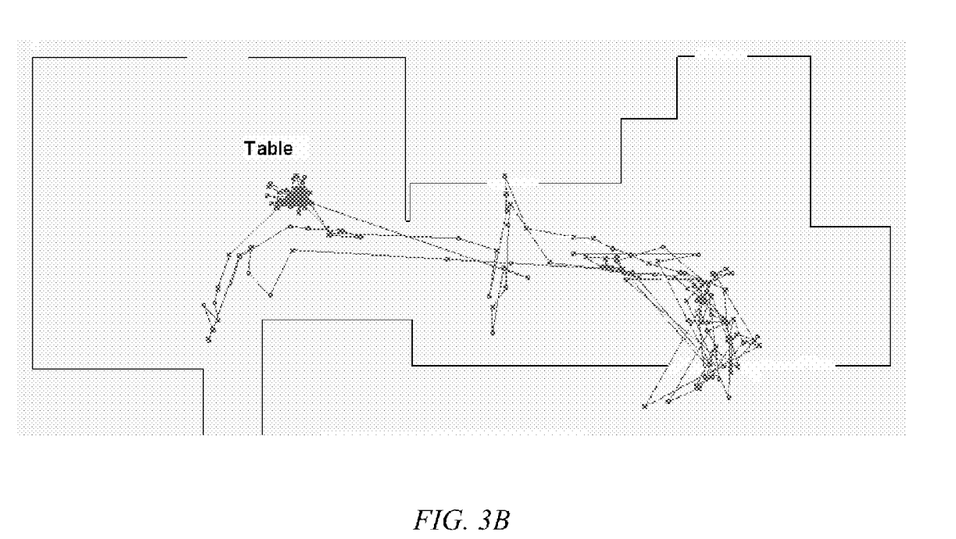
Figure 4A:
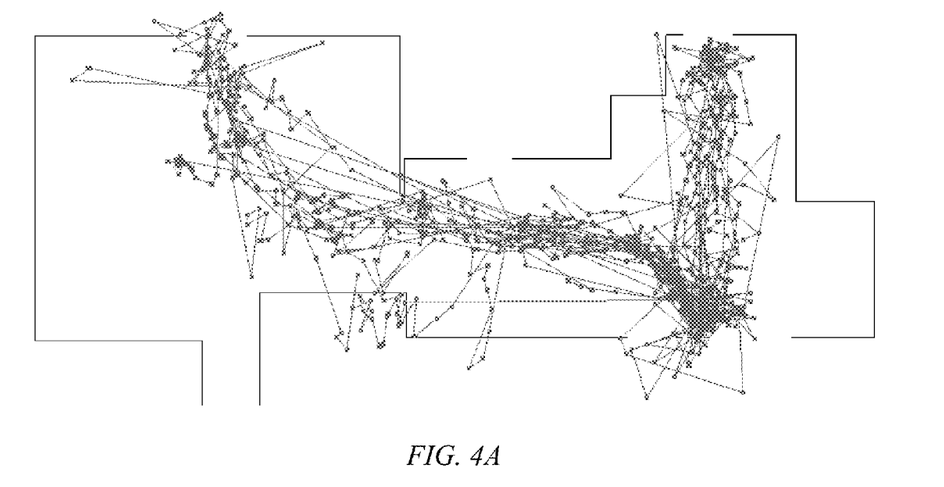
FIGS. 4A and 4B are diagrams of an area used in an example of an application of the present invention each show-ing the paths taken by a second subject on two different days. Each diagram represents the paths taken on a single day.
Figure 4B:
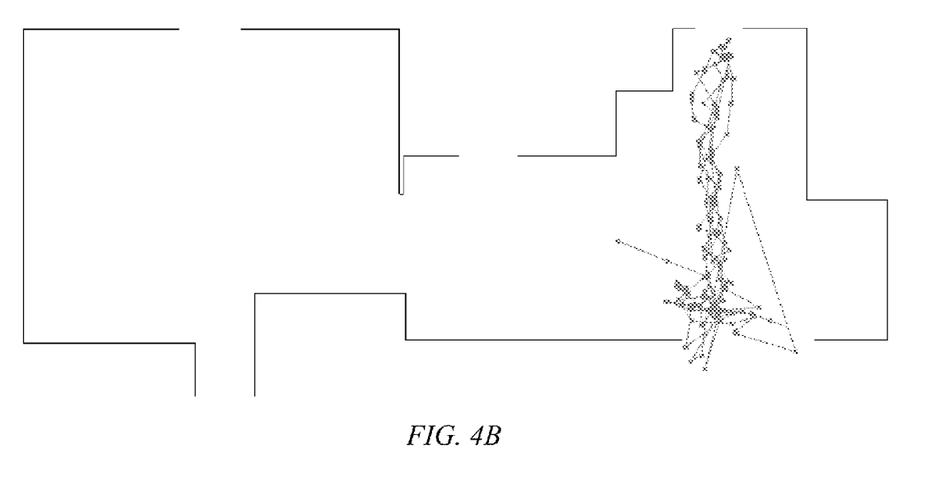

Approximately 1.4 million data points were generated by all subjects completing the protocol. Clearly impossible data were rejected by software filters, leaving 854,336 data points for analysis. Tags whose position did not change for sixty seconds or more were deemed stationary. The first datum recorded thereafter (in response to movement) started a new path, and successive data points were accrued until the tag was again stationary for sixty seconds signifying the end of that path. FIGS. 3A and 3B show the paths taken by a first subject on two different days. FIGS. 4A and 4B show the paths taken by a second subject on the same two days.

Path data for each subject was then analyzed for Fractal D path tortuosity characteristics. Fractal D was estimated using the FractalMean estimator (an extension of the divider estimator) using the program Fractal (V. O. Nams, Detecting oriented movement of animals, *Animal Behavior*, 72, 1197-1203 (2006)). Visual inspection (blindly, without knowing the MMSE scores) of the Fractal D values for the first ten subjects clearly indicated a spatial scale of two to seven best differentiated the subjects, and this spatial scale was selected for all subsequent subjects and all analyses conducted. Fractal D was estimated for each path generated by each subject and then averaged to produce a single score for each individual.

Figure 5:
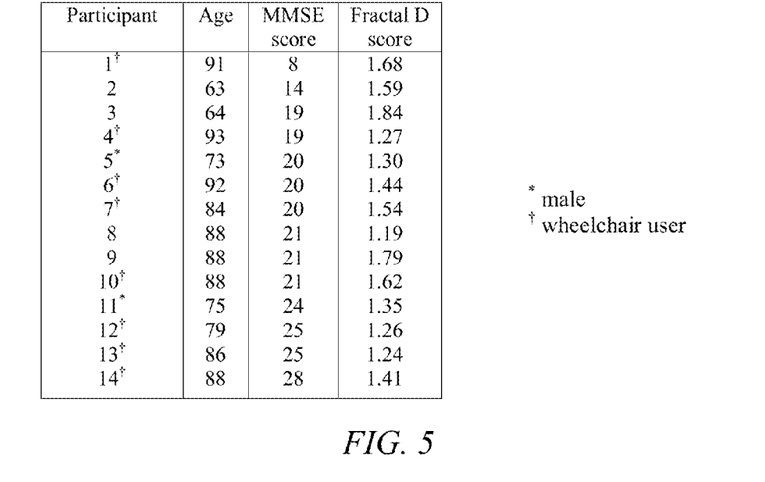
FIG. 5 is a table summarizing the results of an evaluation of the cognitive function of elderly human subjects living in an Assisted Living Facility in accordance with an embodiment of the present invention. The table shows the participants' ages, sex, means of locomotion, Mini Mental State Exam (MMSE) scores, and Fractal D scores. A lower MMSE score denotes lower cognitive functioning and MMSE was negatively and significantly correlated to Fractal D ($r=-0.47$ $p<0.05$).

All participants but one were administered the MMSE after completing the protocol. One subject died before the test could be administered but had an MMSE administered within two months of the beginning of the study, and this measure was used as a proxy; the scores appear in the table in FIG. 5. MMSE scores did not differ statistically by method of ambulation (wheelchair vs. walker-ambulatory; $t=-0.43$ $df=13$, $p=0.67$).

The median number of location data points obtained per subject was 43,397, with a range of 3,727 to 230,241 reflecting large individual differences in both time spent by the subjects in the monitored area and their rate of travel. The numbers of paths per subject also varied considerably from 141 to 1,030 with a mean of 530.2. The Pearson product moment correlation coefficient between MMSE and Fractal D was found to be $-0.47$, which was statistically significant ($p<0.05$). This supports the hypothesis that lower MMSE would predict more variable walking paths.

Figure 6:
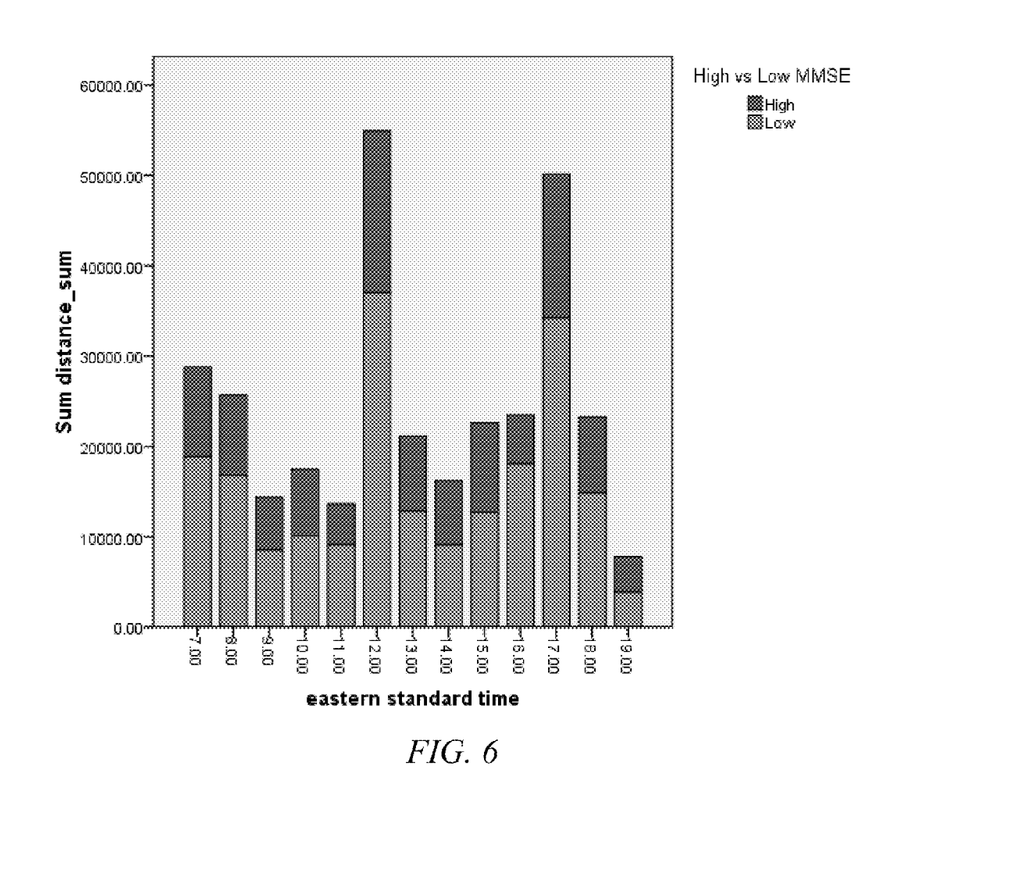
FIG. 6 is a graph showing the results of a diurnal variability analysis of monthly distance travelled in meters. The cumulative distance traveled for subjects above and below the median MMSE value of 20.5, by hour of the day was calculated. Subjects were most active during the noon hour and at approximately 5 p.m. each day. A two-way (high vs. low MMSE) by time (hour) mixed model analysis of variance was performed on these data to evaluate the effects of MMSE level on activity levels at each hour of the day

A Diurnal Variability Analysis was also performed on the data. The cumulative distance traveled for all subjects and for subjects above and below the median MMSE value of 20.5, by hour of the day was calculated, as shown in the graph in FIG. 6. A two-way (high vs. low MMSE) by time (13-hour) mixed model analysis of variance was performed on these data to evaluate the effects of MMSE level on activity levels at each hour of the day. Neither the F-test for MMSE status ($F=1.1$, $MS=45438744$, $df=1$, $p=0.31$), or time ($F=1.7$, $MS=13343711$, $df=12$, $p=0.07$) were significant, neither was the groups-time interaction ($F=0.33$, $MS=2618257$, $df=12$, $p=0.98$).

While the results support findings by other researchers who have demonstrated relationships between movement variability and dementia using conventional methods to analyze gait and balance, those techniques require skilled personnel to administer them under controlled conditions. In contrast, the present method gathers data from free movements, not only those taken while walking in a straight line or under contrived circumstances, and within an individual's home environment, and is minimally intrusive on normal routines. The method also successfully predicted MMSE values irrespective of type of ambulation (ambulatory, walker, or wheelchair) precisely because of its reliance on path variability (tortuosity) and not on distance travelled, which failed to differentiate the participants. Furthermore, the instrumentation need not be installed in an entire facility but only in areas such as atriums through which persons routinely pass on their way to other locations.

II. Military Training Applications

The tracking and AI functions of the present invention are also applicable to training scenarios for military personnel. Movement information in battlefield simulations can be a key differentiator of successful from unsuccessful recruits. The failures to negotiate terrain, incorrect target identification, or delayed response in meeting a threat situation are identifiable features that are detected by the system. The system also makes recommendations to supervisors based on performance of those candidates that showed the most promise and identifies those which may be better reassigned to other tasks.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention, which, as a matter of language, might be said to fall there between.

What is claimed is:

1. A method of tracking and analyzing movement of human subjects, the method comprising:
   providing a plurality of tracking technology sensors;
   placing the plurality of sensors within a designated space;
   determining an origin location within the space;
   providing a plurality of tracking technology transponders, wherein the transponders provide location parameters;
   affixing one of the plurality of transponders to each human subject;
   collecting the location parameters of each human subject from the transponders at predetermined time intervals using the sensors;
   determining a plurality of movement paths for each human subject from the location parameters, wherein each movement path comprises the location parameters from each period of movement of each human subject;
   recording the plurality of movement paths for fractal dimension tortuosity characteristics;
   setting a spatial scale;
   calculating an estimated fractal dimension for each of the plurality of movement paths of each human subject; and
   calculating an average of the estimated fractal dimensions for each of the plurality of movement paths for each subject to produce a single fractal dimension score for each human subject, wherein a high fractal dimension score corresponds to a high likelihood of agitated movement and the greater the value of the fractal dimension score corresponds to the greater degree of agitated movement.

2. The method of claim 1, further comprising:
   removing location parameters that represent impossible movement.

3. The method of claim 1, further comprising:
  removing location parameters that represent movement outside the designated space.

4. The method of claim 1, further comprising:
  removing location parameters that represent non-movement for a predetermined time.

5. The method of claim 1, further comprising:
  correlating the fractal dimension tortuosity characteristics and cognitive status of the human subjects.

6. A method of detecting dementia in human subjects, the method comprising:
  providing a plurality of tracking technology sensors;
  placing the plurality of sensors within a designated space such that the daily movements of the subjects are captured by the sensors;
  determining an origin location within the space;
  providing a plurality of tracking technology transponders, wherein the transponders provide location parameters;
  affixing one of the plurality of transponders to each human subject;
  collecting the location parameters of each human subject from the transponders at predetermined time intervals using the sensors;
  determining a plurality of movement paths for each human subject from the location parameters, wherein each movement path comprises the location parameters from each period of movement of each subject;
  analyzing the plurality of movement paths for fractal dimension tortuosity characteristics;
  choosing the appropriate spatial scale;
  estimating Fractal D fractal dimension for each of the plurality of movement paths of each human subject; and
  calculating an average of the estimated fractal dimensions for each of the plurality of movement paths for each human subject to produce a single fractal dimension score for each human subject, wherein a high fractal dimension score corresponds to a high likelihood of dementia and the greater the value of the fractal dimension score corresponds to the greater degree of dementia.

7. The method of claim 6, wherein an accuracy of the location parameters is within about 20 cm.

8. The method of claim 6, wherein collecting the location parameters occurs about every 0.4 seconds.

9. The method of claim 6, further comprising:
  correlating the fractal dimension tortuosity characteristics and cognitive status of the human subjects.

10. The method of claim 6, further comprising:
  removing location parameters that represent impossible movement.

11. The method of claim 6, further comprising:
  removing location parameters that represent movement outside the designated space.

12. The method of claim 6, further comprising:
  removing location parameters that represent non-movement for a predetermined time.

13. The method of claim 6, wherein the tracking technology is chosen from the group consisting of ultra-wideband radio technology and radio-frequency identification (RFID) technology.

14. The method of claim 6, wherein the transponders provide location parameters in three planes (x, y, and z).

15. The method of claim 1, wherein the tracking technology is chosen from the group consisting of ultra-wideband radio technology and radio-frequency identification (RFID) technology.

16. The method of claim 1, wherein the transponders provide location parameters in three planes (x, y, and z).

* * * * *

UNITED STATES PATENT AND TRADEMARK OFFICE
CERTIFICATE OF CORRECTION

PATENT NO. : 7,978,085 B1
APPLICATION NO. : 12/396002
DATED : July 12, 2011
INVENTOR(S) : Kearns et al.

Page 1 of 1

It is certified that error appears in the above-identified patent and that said Letters Patent is hereby corrected as shown below:

Column 1, the portion of the Statement of Government Interest reading "Grant No. 071123 ARG-2007-34 (Kearns USF) awarded by the Johnnie B. Byrd, Sr. Alzheimer's Institute" should be changed to --Grant No. HS018205 awarded by the National Institutes of Health--

Signed and Sealed this
Nineteenth Day of February, 2013

Teresa Stanek Rea
*Acting Director of the United States Patent and Trademark Office*